United States Patent [19]
Aoki et al.

[11] Patent Number: 5,661,000
[45] Date of Patent: Aug. 26, 1997

[54] SERINE PROTEASE AND SERINE PROTEASE GENE

[75] Inventors: Yosuke Aoki, Tochigi; Kiyoshi Okano, Kamakura; Masanobu Naruto, Kamakura; Hirohiko Shimizu, Kamakura; Haruji Nakamura, Hiratsuka, all of Japan

[73] Assignee: Toray Industries, Inc., Japan

[21] Appl. No.: 385,230

[22] Filed: Feb. 8, 1995

Related U.S. Application Data

[63] Continuation of Ser. No. 32,454, Mar. 17, 1993, abandoned, which is a continuation of Ser. No. 735,187, Jul. 24, 1991, abandoned, which is a continuation of Ser. No. 290,049, filed as PCT/JP88/00205, Feb. 26, 1988 published as WO88/06621, Sep. 7, 1988, abandoned.

[30] Foreign Application Priority Data

Mar. 5, 1987 [JP] Japan ................................. 62-50676
Sep. 9, 1987 [JP] Japan ................................. 62-225540

[51] Int. Cl.$^6$ ........................... C12P 21/06; C07H 21/04; C12N 15/63; C12N 9/50
[52] U.S. Cl. .................. 435/69.1; 435/69.8; 435/172.3; 435/219; 435/320.1; 536/23.1; 935/14; 935/36; 935/48
[58] Field of Search ................... 435/69.1, 69.8, 435/172.3, 219, 320.1; 536/23.1; 935/14, 36, 48

[56] References Cited

U.S. PATENT DOCUMENTS 4,711,843 12/1987 Chang ........................................ 935/47
4,963,495 10/1990 Chang et al. .............................. 935/48

OTHER PUBLICATIONS

Okano et al, Molecular Cloning of Complementary DNA for Human Medullasin: An Inflammatory Serine Protease in Bone Marrow Cells, J. Biochem. 102, 13–16 (1978).

Nakamura et al, Nucleotide Sequences of Human Bone Marrow Serine Protease (Medullasin) Gene, vol. 15 No. 22 1987.
Farley et al, Molecular Cloning of Human Neutrophil Elastase, vol. 369, Suppl., pp. 3–7, May 1988.
Bode et al. (1986), EMBO J., vol. 5, pp. 2453–2458.
Crocker et al. (1984), J. Clin. Pathol., vol. 37, pp. 1114–1118.
Dunn et al. (1985), Anal. Biochem., vol. 150, pp. 18–25.
Damiano et al. (1986), J. Clin. Invest., vol. 78, pp. 482–493.
Young et al. (1983), Science, vol. 222, pp. 778–782.
Heck et al (1985) "Isolation . . . of human elastase," Anal. Biochem, vol. 149, pp. 153–162.
Baugh et al (1976) "Human leukocyte granule elastase," Biochem, vol. 15, pp. 836–841.
Aoki (1978) "New Protease in mitochondria of Bone marrow cells," JBC, vol. 253, pp. 2026–2032.
Suggs et al (1981) "Use of synthetic oligonucleotides as probes," PNAS, vol. 78, pp.6613–6617.
Lawn et al (1978) "Isolation of genes from cloned library of human DNA," Cell, vol. 15, p. 1157.
Greenberg et al (1984) "Nucleotide sequence of the gene encoding human ANF," Nature, vol. 312, pp. 656–658.

*Primary Examiner*—Douglas W. Robinson
*Assistant Examiner*—Thanda Wai
*Attorney, Agent, or Firm*—Austin R. Miller

[57] ABSTRACT

The present invention offers the serine protease exhibiting a biological activity which a polypeptide having an amino acid sequence shown in FIG. 1 shows, the serine protease precursor where a cleavable peptide or signal peptide connects with the N-terminal of the said serine protease, and the gene encoding them. The serine protease being useful in medical treatment fields can be manufactured in large quantities by the present invention.

Moreover, the present invention offers the DNA sequence coding a transcription controlling region contained in the chromosomal gene of the serine protease of a human myeloid cell. This sequence is the transcription controlling region being necessary for the gene expression being specific to a human leukocyte or erythrocyte.

15 Claims, 17 Drawing Sheets

1
Ile-Val-Gly-Gly-Arg-Arg-Ala-Arg-Pro-His- Ala-Trp-Pro-Phe-Met-Val-Ser-Leu-Gln-Leu

21
Arg-Gly-Gly-His-Phe-Cys-Gly-Ala-Thr-Leu- Ile-Ala-Pro-Asn-Phe-Val-Met-Ser-Ala- Ala

41
His-Cys-Val-Ala-Asn-Val-Asn-Val-Arg-Ala- Val-Arg-Val-Val-Leu-Gly-Ala-His-Asn-Leu

61
Ser-Arg-Arg-Glu-Pro-Thr-Arg-Gln-Val-Phe-Ala-Val-Gln-Arg-Ile-Phe-Glu-Asn-Gly- Tyr

81
Asp-Pro-Val-Asn-Leu-Leu-Asn-Asp-Ile-Val- Ile-Leu-Gln-Leu-Asn-Gly-Ser-Ala-Thr-Ile

101
Asn-Ala-Asn-Val-Gln-Val-Ala-Gln-Leu-Pro- Ala-Gln-Gly-Arg-Arg-Leu-Gly-Asn-Gly- Val

121
Gln-Cys-Leu-Ala-Met-Gly-Trp-Gly-Leu-Leu-Gly-Arg-Asn-Arg-Gly-Ile-Ala-Ser-Val- Leu

141
Gln-Glu-Leu-Asn-Val-Thr-Val-Val-Thr-Ser- Leu-Cys-Arg-Arg-Ser-Asn-Val-Cys-Thr-Leu

161
Val-Arg-Gly-Arg-Gln-Ala-Gly-Val-Cys-Phe- Gly-Asp-Ser-Gly-Ser-Pro-Leu-Val-Cys- Asn

181
Gly-Leu-Ile-His-Gly-Ile-Ala-Ser-Phe-Val- Arg-Gly-Gly-Cys-Ala-Ser-Gly-Leu-Tyr-Pro

201
Asp-Ala-Phe-Ala-Pro-Val-Ala-Gln-Phe-Val- Asn-Trp-Ile-Asp-Ser-Ile-Ile-Gln-Arg- Ser 221                                                                                      238
Glu-Asp-Asn-Pro-Cys-Pro-His-Pro-Arg-Asp-Pro-Asp-Pro-Ala-Ser-Arg-Thr-His

*Fig. 1*

```
        10          20          30          40          50          60
GTGGGGGGCC  GGCGAGCGCG  GCCCCACGCG  TGGCCCTTCA  TGGTGTCCCT  GCAGCTGCGC 70          80          90         100         110         120
GGAGGCCACT  TCTGCGGCGC  CACCCTGATT  GCGCCCAACT  TCGTCATGTC  GGCCGCGCAC 130         140         150         160         170         180
TGCGTGGCGA  ATGTAAACGT  CCGCGCGGTG  CGGGTGGTCC  TGGGAGCCCA  TAACCTCTCG 190         200         210         220         230         240
CGGCGGGAGC  CCACCCGGCA  GGTGTTCGCC  GTGCAGCGCA  TCTTCGAAAA  CGGCTACGAC 250         260         270         280         290         300
CCCGTAAACT  TGCTCAACGA  CATCGTGATT  CTCCAGCTCA  ACGGGTCGGC  CACCATCAAC 310         320         330         340         350         360
GCCAACGTGC  AGGTGGCCCA  GCTGCCGGCT  CAGGGACGCC  GCCTGGGCAA  CGGGGTGCAG 370         380         390         400         410         420
TGCCTGGCCA  TGGGCTGGGG  CCTTCTGGGC  AGGAACCGTG  GGATCGCCAG  CGTCCTGCAG 430         440         450         460         470         480
GAGCTCAACG  TGACGGTGGT  GACGTCCCTC  TGCCGTCGCA  GCAACGTCTG  CACTCTCGTG 490         500         510         520         530         540
AGGGGCCGGC  AGGCCGGCGT  CTGTTTCGGG  GACTCCGGCA  GCCCCTTGGT  CTGCAACGGG 550         560         570         580         590         600
CTAATCCACG  GAATTGCCTC  CTTCGTCCGG  GGAGGCTGCG  CCTCAGGGCT  CTACCCCGAT 610         620         630         640         650         660
GCCTTTGCCC  CGGTGGCACA  GTTTGTAAAC  TGGATCGACT  CTATCATCCA  ACGCTCCGAG 670         680         690         700         710
GACAACCCCT  GTCCCCACCC  CCGGGACCCG  GACCCGGCCA  GCAGGACCCA  C
```

*Fig.2*

1
Ile-Val-Gly-Gly-Arg-Arg-Ala-Arg-Pro-His-

11
Ala-Trp-Pro-Phe-Met-Val-Ser-Leu-Gln-Leu

21
Arg-Gly-Gly-His-Phe-(Cys)-Gly-Ala-Thr-Leu-

31
Ile-Ala-Pro-Asn-Phe-Val-Met-(Ser)-Ala-Ala 41                                         49
His-Cys-Val-Ala-Asn-Val-Asn-Val-Arg

Fig. 3

```
     10         20         30         40         50         60
GAATTCCGTG GGGGGCCGGC GAGCGCGGCC CCACGCGTGG CCCTTCATGG TGTCCCTGCA 70         80         90        100        110        120
GCTGCGCGGA GGCCACTTCT GCGGCGCCAC CCTGATTGCG CCCAACTTCG TCATGTCGGC 130        140        150        160        170        180
CGCGCACTGC GTGGCGAATG TAAACGTCCG CGCGGTGCGG GTGGTCCTGG GAGCCCATAA 190        200        210        220        230        240
CCTCTCGCGG CGGGAGCCCA CCCGGCAGGT GTTCGCCGTG CAGCGCATCT TCGAAAACGG 250        260        270        280        290        300
CTACGACCCC GTAAACTTGC TCAACGACAT CGTGATTCTC CAGCTCAACG GGTCGGCCAC 310        320        330        340        350        360
CATCAACGCC AACGTGCAGG TGGCCCAGCT GCCGGCTCAG GGACGCCGCC TGGGCAACGG 370        380        390        400        410        420
GGTGCAGTGC CTGGCCATGG GCTGGGGCCT TCTGGGCAGG AACCGTGGGA TCGCCAGCGT 430        440        450        460        470        480
CCTGCAGGAG CTCAACGTGA CGGTGGTGAC GTCCCTCTGC CGTCGCAGCA ACGTCTGCAC 490        500        510        520        530        540
TCTCGTGAGG GGCCGGCAGG CCGGCGTCTG TTTCGGGGAC TCCGGCAGCC CCTTGGTCTG 550        560        570        580        590        600
CAACGGGCTA ATCCACGGAA TTGCCTCCTT CGTCCGGGGA GGCTGCGCCT CAGGGCTCTA 610        620        630        640        650        660
CCCCGATGCC TTTGCCCCGG TGGCACAGTT TGTAAACTGG ATCGACTCTA TCATCCAACG 670        680        690        700        710        720
CTCCGAGGAC AACCCCTGTC CCCACCCCCG GGACCCGGAC CCGGCCAGCA GGACCCACTG 730        740        750        760        770        780
AGAAGGGCTG CCCGGGTCAC CTCAGCTGCC CACACCCACA CTCTCCAGCA TCTGGCACAA 790        800        810        820
TAAACATTCT CTGTTTTGTA AAAAAAGGAA TTC
```

Fig. 4

1
Val-Gly-Gly-Arg-Arg-Ala-Arg-Pro-His-Ala-Trp-Pro-Phe-Met-Val-Ser-Leu-Gln-Leu-Arg

21
Gly-Gly-His-Phe-Cys-Gly-Ala-Thr-Leu-Ile-Ala-Pro-Asn-Phe-Val-Met-Ser-Ala-Ala-His

41
Cys-Val-Ala-Asn-Val-Asn-Val-Arg-Ala-Val-Arg-Val-Val-Leu-Gly-Ala-His-Asn-Leu-Ser

61
Arg-Arg-Glu-Pro-Thr-Arg-Gln-Val-Phe-Ala-Val-Gln-Arg-Ile-Phe-Glu-Asn-Gly-Tyr-Asp

81
Pro-Val-Asn-Leu-Leu-Asn-Asp-Ile-Val-Ile-Leu-Gln-Leu-Asn-Gly-Ser-Ala-Thr-Ile-Asn

101
Ala-Asn-Val-Gln-Val-Ala-Gln-Leu-Pro-Ala-Gln-Gly-Arg-Arg-Leu-Gly-Asn-Gly-Val-Gln

121
Cys-Leu-Ala-Met-Gly-Trp-Gly-Leu-Leu-Gly-Arg-Asn-Arg-Gly-Ile-Ala-Ser-Val-Leu-Gln

141
Glu-Leu-Asn-Val-Thr-Val-Val-Thr-Ser-Leu-Cys-Arg-Arg-Ser-Asn-Val-Cys-Thr-Leu-Val

161
Arg-Gly-Arg-Gln-Ala-Gly-Val-Cys-Phe-Gly-Asp-Ser-Gly-Ser-Pro-Leu-Val-Cys-Asn-Gly

181
Leu-Ile-His-Gly-Ile-Ala-Ser-Phe-Val-Arg-Gly-Gly-Cys-Ala-Ser-Gly-Leu-Tyr-Pro-Asp

201
Ala-Phe-Ala-Pro-Val-Ala-Gln-Phe-Val-Asn-Trp-Ile-Asp-Ser-Ile-Ile-Gln-Arg-Ser-Glu 221                                                                            237
Asp-Asn-Pro-Cys-Pro-His-Pro-Arg-Asp-Pro-Asp-Pro-Ala-Ser-Arg-Thr-His

*Fig. 5*

-29
Met Thr Leu Gly Arg Arg Leu Ala Cys Leu Phe Leu Ala Cys Val Leu Pro Ala Leu

-10                                              1
Leu Leu Gly Gly Thr Ala Leu Ala Ser Glu  Ile Val Gly Gly Arg Arg Ala Arg Pro His

11
Ala Trp Pro Phe Met Val Ser Leu Gln Leu Arg Gly Gly His Phe Cys Gly Ala Thr Leu

31
Ile Ala Pro Asn Phe Val Met Ser Ala Ala  His Cys Val Ala Asn Val Asn Val Arg Ala

51
Val Arg Val Val Leu Gly Ala His Asn  Leu Ser Arg Arg Glu Pro Thr Arg Gln Val Phe

71
Ala Val Gln Arg Ile Phe Glu Asn Gly Tyr  Asp Pro Val Asn Leu Leu Asn Asp Ile Val

91
Ile Leu Gln Leu Asn Gly Ser Ala Thr Ile  Asn Ala Asn Val Gln Val Ala Gln Leu Pro

111
Ala Gln Gly Arg Arg Leu Gly Asn Gly  Val Gln Cys Leu Ala Met Gly Trp Gly Leu Leu

131
Gly Arg Asn Arg Gly Ile Ala Ser Val  Leu Gln Glu Leu Asn Val Thr Val Val Thr Ser

151
Leu Cys Arg Arg Ser Asn Val Cys Thr Leu Val Arg Gly Arg Gln Ala Gly Val Cys Phe

171
Gly Asp Ser Gly Ser Pro Leu Val Cys  Asn Gly Leu Ile His Gly Ile Ala Ser Phe Val

191
Arg Gly Gly Cys Ala Ser Gly Leu Tyr  Pro Asp Ala Phe Ala Pro Val Ala Gln Phe Val

211
Asn Trp Ile Asp Ser Ile Ile Gln Arg  Ser Glu Asp Asn Pro Cys Pro His Pro Arg Asp 231                      238
Pro Asp Pro Ala Ser Arg Thr His

*Fig. 6*

|  10 | 20 | 30 | 40 | 50 | 60 |
|---|---|---|---|---|---|
| GCACGGAGGG | GCAGAGACCC | CGGAGCCCCA | GCCCCACCAT | GACCCTCGGC | CGCCGACTCG |
| 70 | 80 | 90 | 100 | 110 | 120 |
| CGTGTCTTTT | CCTCGCCTGT | GTCCTGCCGG | CCTTGCTGCT | GGGGGGCACC | GCGCTGGCCT |
| 130 | 140 | 150 | 160 | 170 | 180 |
| CGGAGATTGT | GGGGGGCCGG | CGAGCGCGGC | CCCACGCGTG | GCCCTTCATG | GTGTCCCTGC |
| 190 | 200 | 210 | 220 | 230 | 240 |
| AGCTGCGCGG | AGGCCACTTC | TGCGGCGCCA | CCCTGATTGC | GCCCAACTTC | GTCATGTCGG |
| 250 | 260 | 270 | 280 | 290 | 300 |
| CCGCGCACTG | CGTGGCGAAT | GTAAACGTCC | GCGCGGTGCG | GGTGGTCCTG | GGAGCCCATA |
| 310 | 320 | 330 | 340 | 350 | 360 |
| ACCTCTCGCG | GCGGGAGCCC | ACCCGGCAGG | TGTTCGCCGT | GCAGCGCATC | TTCGAAAACG |
| 370 | 380 | 390 | 400 | 410 | 420 |
| GCTACGACCC | CGTAAACTTG | CTCAACGACA | TCGTGATTCT | CCAGCTCAAC | GGGTCGGCCA |
| 430 | 440 | 450 | 460 | 470 | 480 |
| CCATCAACGC | CAACGTGCAG | GTGGCCCAGC | TGCCGGCTCA | GGGACGCCGC | CTGGGCAACG |
| 490 | 500 | 510 | 520 | 530 | 540 |
| GGGTGCAGTG | CCTGGCCATG | GGCTGGGGCC | TTCTGGGCAG | GAACCGTGGG | ATCGCCAGCG |
| 550 | 560 | 570 | 580 | 590 | 600 |
| TCCTGCAGGA | GCTCAACGTG | ACGGTGGTGA | CGTCCCTCTG | CCGTCGCAGC | AACGTCTGCA |
| 610 | 620 | 630 | 640 | 650 | 660 |
| CTCTCGTGAG | GGGCCGGCAG | GCCGGCGTCT | GTTTCGGGGA | CTCCGGCAGC | CCCTTGGTCT |
| 670 | 680 | 690 | 700 | 710 | 720 |
| GCAACGGGCT | AATCCACGGA | ATTGCCTCCT | TCGTCCGGGG | AGGCTGCGCC | TCAGGGCTCT |
| 730 | 740 | 750 | 760 | 770 | 780 |
| ACCCCGATGC | CTTTGCCCCG | GTGGCACAGT | TTGTAAACTG | GATCGACTCT | ATCATCCAAC |
| 790 | 800 | 810 | 820 | 830 | 840 |
| GCTCCGAGGA | CAACCCCTGT | CCCCACCCCC | GGGACCCGGA | CCCGGCCAGC | AGGACCCACT |
| 850 | 860 | 870 | 880 | 890 | 900 |
| GAGAAGGGCT | GCCCGGGTCA | CCTCAGCTGC | CCACACCCAC | ACTCTCCAGC | ATCTGGCACA |
| 910 | 920 | | | | |
| ATAAACATTC | TCTGTTTTGT | | | | |

Fig. 7

```
          10         20         30         40         50         60
5   TTGTCAGAGCCCCAGCTGGTGTCCAGGGACTGACCGTGAGCCTGGGTGAA AGTGAGTTCC
          70        80         90        100        110        120
    CCGTTGGAGG CACCAGACGAGGAGAGGATGGAAGGCCTGG CCCCCAAGAATGAGCCCTGA
         130        140        150        160        170        180
    GGTTCAGGAGCGGCTGGAGTGAGCCGCCCC CAGATCTCCGTCCAGCTGCGGGTCCCAGAG
         190        200        210        220        230        240
    GCCTGGGTTA CACTCGGAGCTCCTGGGGGA GGCCCTTGACGTGCTCAGTT CCCAAACAGG
         250        260        270        280        290        300
    AACCCTGGGAAGGACCAGAG AAGTGCCTATTGCGCAGTGAGTGCCCGACA CAGCTGCATG
         310        320        330        340        350        360
    TGGCCGGTATCACAGGGCCC TGGGTAAACTGAGGCAGGCG ACACAGCTGCATGTGGCCGG
         370        380        390        400        410        420
    TATCACAGGGCCCTGGGTAAACTGAGGCAG GCGACACAGCTGCATGTGGC CGGTATCACA
         430        440        450        460        470        480
    GGGCCCTGGG TAAACTGAGG CAGGCGACAC AGCTGCATGTGGCCGGTATCACAGGGCCCT
         490        500        510        520        530        540
    GGGTAAACTGAGGCAGGCGA CACAGCTGCATGTGGCCGGTATCACGGGGC CCTGGATAAA
         550        560        570        580        590        600
    CAGAGGCAGG CGAGGCCACC CCCATCAAGT CCCTCAGGTCTAGGTTTGGCCAGGTTTGGA
         610        620        630        640        650        660
    AAAACACAGCAACGCTCGGTAAATCTGAATTTCGGGTAAG TATATCCTGG GCCTCATTTG
         670        680        690        700        710        720
    GAAGAGACTT AGATTAAAAA AAAAACGTCG AGACCAGCCCGGCCAACACG TGAAACCCCG
         730        740        750        760        770        780
    TCTCTACTAAAAATACAAAA AATTAGCCAGGCGCAGTGCTCACGCCTGTG ATCCCAGCAC
         790        800        810        820        830        840
    TCTGGGAGGT GAGGCAGGCG GATCACCCGAGGTCAGCTGT TCAAGACCAGCCTGGCCGAG
         850        860        870        880        890        900
    TGGGCGAAAC ACTGTCTCTACTACAAATAC AAAAATTAGCCGGGAGTGGAGGCAGGTGCC
         910        920        930        940        950        960
    TGTAATCTCA GCTATTCAGGAGGCTGAGGC AGGAGAATCA CTTGAACCTGGGAGGCGGAG
         970        980        990       1000       1010       1020
    GTTGCCGTGAGCCGGGATCACGCCACCGCA CTCCAGCCTGGGCGATAGAG CAAGACTCTG
        1030       1040       1050       1060       1070       1080
    TCTCCAAAAAAATAAATTAA AAAACCCACA TTGATTATCT GACATTTGAATGCGATTGTG
        1090       1100       1110       1120       1130       1140
    CATCCTGAATTTTGTCTGGA GGCCCCACCC GAGCCAATCCAGCGTCTTGT CCCCCTTCTC
        1150       1160       1170       1180       1190       1200
    CCCCTTTTCA TCAACGCCTGTGCCAGGGGAGAGGAAGTGG AGGGCGCTGG CCGGCCGTGG
        1210       1220       1230       1240       1250
    GGCAATGCAACGGCCTCCCAGCACAGGGCTATAAGAGGAGCCGGGCGGGC
```

*Fig. 15*

```
TTGTCAGAGCCCCAGCTGGTGTCCAGGGACTGACCGTGAGCCTGGGTGAAAGTGAGTTCCCCGTTGGAGGCACCAGACGA
GGAGAGGATGGAAGGCCTGGCCCCCAAGAATGAGCCCTGA GGTTCAGGAGCGGCTGGAGTGAGCCGCCCC CAGATCTCCG
TCCAGCTGCG GGTCCCAGAGGCCTGGGTTA CACTCGGAGCTCCTGGGGGAGGCCCTTGACGTGCTCAGTTCCCAAACAGG.
AACCCTGGGAAGGACCAGAGAAGTGCCTATTGCGCAGTGAGTGCCCGACACAGCTGCATG TGGCCGGTAT CACAGGGCCC
TGGGTAAACTGAGGCAGGCGACACAGCTGCATGTGGCCGGTATCACAGGGCCCTGGGTAAACTGAGGCAGGCGACACAGC   400
TGCATGTGGCCGGTATCACAGGGCCCTGGGTAAACTGAGGCAGGCGACACAGCTGCATGTGGCCGGTATCACAGGGCCCT
GGGTAAACTGAGGCAGGCGACACAGCTGCATGTGGCCGGTATCACGGGGCCCTGGATAAACAGAGGCAGG CGAGGCCACC
CCCATCAAGT CCCTCAGGTCTAGGTTTGGCCAGGTTTGGAAAAACACAGCAACGCTCGGTAAATCTGAATTTCGGGTAAG
TATATCCTGG GCCTCATTTGGAAGAGACTTAGATTAAAAAAAAAACGTCGAGACCAGCCCGGCCAACACGTGAAACCCCG
TCTCTACTAAAAATACAAAAAATTAGCCAGGCGCAGTGCTCACGCCTGTGATCCCAGCACTCTGGGAGGTGAGGCAGGCG   800
GATCACCCGA GGTCAGCTGTTCAAGACCAG CCTGGCCGAGTGGGCGAAACACTGTCTCTA CTACAAATACAAAAATTAGC
CGGGAGTGGAGGCAGGTGCCTGTAATCTCAGCTATTCAGGAGGCTGAGGCAGGAGAATCACTTGAACCTGGGAGGCGGAG
GTTGCCGTGA GCCGGGATCACGCCACCGCACTCCAGCCTGGGCGATAGAGCAAGACTCTGTCTCCAAAAAAATAAATTAA
AAAACCCACATTGATTATCTGACATTTGAATGCGATTGTGCATCCTGAAT TTTGTCTGGA GGCCCCACCCGAGCCAATCC
AGCGTCTTGTCCCCCTTCTCCCCCTTTTCATCAACGCCTGTGCCAGGGGA GAGGAAGTGGAGGGCGCTGGCCGGCCGTGG   1200
GGCAATGCAA CGGCCTCCCA GCACAGGGCTATAAGAGGAGCCGGGCGGGCACGGAGGGGCAGAGACCCCGGAGCCCCAGC
CCCACCATGACCCTCGGCCGCCGACTCGCG TGTCTTTTCCTCGCCTGTGTCCTGCCGGCCTTGCTGCTGGGGGGTGAGTT
TTTGAGTCCAACCTCCCGCTGCTCCCTCTGTCCCGGGTTCTGTTCCCACCTCTCCATAGAGGGCCCCACC AGTGTGGGTC
CCTCATCCTC ACAGGGGAGGTGCCAGCTGG GACAAGGAGACCAGAAGAGACTGAGGTTCTGAGCGGTGAAGCCACCACCA
GGAGCCCAGA GTTGGGGTTT GAAAACCGGG GAGGGGGGGGTGGCAGGTCGCCCTCTGGG TTCAAGTCCA GGTCTGTCTG   1600
TGCCTTGGAG GGGCACCGTGGGGAGGTCCCTTTGCCTCTCCGTGCCTCAG TTTCCTCATC TGAACAACAG GGGTGCGAAC
GGCCCCGATC CCGTGGGTTC CCGGTGGGGGATCCAGAGGC CCCGTGGCCG GGAGGGGACA GGCTCCTTGGCAGGCACTCA
GCACCCGCAC CCGGTGTGTC CCCAGGCACC GCGCTGGCCTCGGAGATTGT GGGGGGCCGGCGAGCGCGGCCCACGCGTG
GCCCTTCATG GTGTCCCTGC AGCTGCGCGGAGGCCACTTC TGCGGCGCCACCCTGATTGC GCCCAACTTC GTCATGTCGG
CCGCGCACTG CGTGGCGAATGTGTGAGTAGCCGGGAGTGTGCGCGCCCGGCTCGGACCCC GCGTCCCGGT CTGTGAGGTG   2000
GGTGGGGGAGGCCGGGGCCGGGGCTGCTGGCGGGGGGGGGTCCGTCCAG GGCCCGCGGGGCCCCTCGAG CACCTTCGCC
CTCAGGCCCG TCGCCGGATG GGGACGACAA GGCGCGGCTGAGCCCCGACC CCCGGGGCCGCCCCTGAGCC CCGCCTCTCC
CTCTTTTGGCAGAAACGTCCGCGCGGTGCGGGTGGTCCTGGGAGCCCATAACCTCTCGCGGCGGGAGCCCACCCGGCAGG
TGTTCGCCGTGCAGCGCATCTTCGAAAACGGCTACGACCCCGTAAACTTGCTCAACGACATCGTGATTCTCCAGGTGCCG
CCGGGCGGGCGGGGCGAGGGCGGAGGCCAGAGGCCTGGGGAGGGTGGAGGCCTGGGAGGGTGGAGGCTGCGACGGAG   2400
GGGCGCGTCGGGGCCGCTCGTGGGGACCTGGGGTGGCATCGTGGGCTGGGTGGTCCCCTC TCCGCGCCTC GGTCTGCACC
TCTGTGAAACGGGAAAATACCCGCCATGGGCCGTTGAGGGGTTAAATGAGATCCTGCAGGGAGGCCCCGATCTGCTGTCA
ATCAACAAAC TTACTGAGAAGGGAGGCCCCGATCTGTTGTCAATCAACAA ACTTACTGAGAAGGGAGGCC CCGATCTGTT
GTCAATCAAC AAACTTACTG AGAAGGGAGGCCCCGATCTG CTGTCAATCA ACAAACTTAC TGAGAAGGGAGGCCCCGATG
```

*Fig. 16A*

```
TTGTCAATCA ACAAACTTAC TGAGAAGGGAGGCCCCGATC TGCTGTCAATCAACCAAACT TACTGAGAAGGGAGGCCCCG  2800
ATCTGCTGTCAATCATCAAA CTTACTGAGAAGGGAGGCCCCGATCTGCTGTCAATCAACA AAACTTACTGA GAAGGGAGGC
CCCCGATCTGTTGTCAATCA ACAAACTTAC TGAGAAGGGAGGCCCCGATC TGCTGTCAATCAACAAACTT ACTGAGATTC
TGTGTGTCTCTCCATTCACC AGTCCTGTGG CCCAGGGCAGGGGCCGCCTC TGTCTTTGGGAAAAGGGGCAAAAGTCCCCA
CCTTTCCACC CCTGTCCGCGGCTTGCAGTTCTGGTTATTT CCTGGGCGCCGGGCCCCGTGGCTCAGGCCTGTCATCCCAG
CACTTTGGGAGGCTGAGGCGGGTGGATCACGAGGTCAGGTGTTCGAGACC AGCCTGAGCA ACATAGTGAA ACCCCGTCTC  3200
TACTAAAATACACAAAAAAAAAATTAGCCG AGTGTGGTTG TGGGTGCCTGTAATGCCAAC TACTCAGGAGGCTGAGGAAG
GAGAATCGCTTGAACCCCGGAGGCGGAGATTGCAGTGAGCTGAGATCACA CCACTGCACT CCAGCCTGGGTCTCAAAAAA
AAAAAAAAAGATTCCTCCCT GGGAAGGGTTAGAGGGAGAGTTTCCTTGTC ACTAAGTTTT CTCATAGCTC TCACCCAGTG
CAGTGGCGCGATCGCAGCTCACTACACCTC CATCTCCTGGGCTCAAGCCACCCTCTCAGC TTGGAATGGGGGGTAGCTGG
AACCACAGGTGCCACCACGTGGTCCACCACGTCTGGCTAATATATATATATACACACACA CATACATATATTATAAATAA  3600
TAAATATATATTTTTATTTAAATAAAATATATAATATTTATAATTATTTTATAATTATAATAATATTTATATAATTATAAA
TATCATTTATAATTATAATATTTATTATTTTATAAAATAATAAATATAAAATATATAAAAATATTTTTATAAATAATAAA
ATATATATATACACACATATATATATATTTTTTGAGACAAGTCTCGCTCTGTCGCCCAGGCTGGAGCGCA GTGCACAATC
TCACTCACTG CACCTCCGCCTCCCAGGTTCAAGCGATTCT CCTGCCTCAGCCTCCCAGGTAGCTGGGACT ACAGGCGCCC
GCCACCACGCCTGGCTAATT TTTGGTATTGTTAGTAGAGA CGGGGTTTAACCATGTTAGCCAGGATGGTC TTGATCTCCT  4000
GACCTTTTGA TTGGCCCACCTCAGCCTCCC AAAATGCTGGGATTATAGGCGTGAGCACCGCACCTGGCAATTTTTTTTTA
TTATTTTTGTAGACATGGGGCTTTGCCACA TTGCCCAGGCTGGTCTTGAATGCCTGGCCTGGCCTAAGTG ATCCTCCTGC
CTCGCCCTCCCAAAGTGCTGGGCTTACAAGCATGAGCCACCGCGCCCGGCTGTAGTTTTT TTGTTAACTGAGCACCTACT
GCTTCCTGCACTCAAGCCACATCCAGGGACAACCTCCAAC GCCCTGAGCCTTGGTGACGGCTCCCACTCT ACAGATGGGG
AAACCGAGGCTTGCCTTGGGGAGCAGAGTGTGGGGTGGGTATCCTGCCCT GCAGGATCCCAGAACCACAG TGGAACCTGA  4400
GATGGGGAAACTGAGGCCCGGAGAGGGGAGGGTCATCATCACTGCCCCGTGTGACGCGCTGACGATCTGTCCCCACCGCC
ACAGCTCAAC GGGTCGGCCACCATCAACGC CAACGTGCAGGTGGCCCAGCTGCCGGCTCAGGGACGCCGCCTGGGCAACG
GGGTGCAGTGCCTGGCCATGGGCTGGGGCCTTCTGGGCAGGAACCGTGGGATCGCCAGCGTCCTGCAGGAGCTCAACGTG
ACGGTGGTGACGTCCCTCTG CCGTCGCAGC AACGTCTGCA CTCTCGTGAGGGGCCGGCAGGCCGGCGTCT GTTTCGTACG
TGCCCTGGGTGTCCCTCTGC TCCCCACCCGCTCCCAGCCCGGTACTGCAGCAACAGGCACCGTGGCTAGACCCTAGGATG  4800
GGACTTCCCAACCCTGACAC GTCGGCGGGCAGGTGGGCAGGGCCTCGCAGTCCAGCTTCC CCACCTTGTC TGCCTCCACA
GGGGGACTCCGGCAGCCCCT TGGTCTGCAACGGGCTAATCCACGGAATTGCCTCCTTCGT CCGGGGAGGCTGCGCCTCAG
GGCTCTACCC CGATGCCTTT GCCCCGGTGGCACAGTTTGT AAACTGGATC GACTCTATCA TCCAACGCTC CGAGGACAAC
CCCTGTCCCC ACCCCCGGGA CCCGGACCCG GCCAGCAGGA CCCACTGAGAAGGGCTGCCC GGGTCACCTC AGCTGCCCAC
ACCCACACTC TCCAGCATCT GGCACAATAAACATTCTCTG TTTTGTAGAATGTGTTTGATGCTCCTTGGCTGTGTGATTG  5200
GGTGTTGAAAATGGTCAGTAGGTCGGGCGTGGTGGCTCACACCTGTAATC CCAGCACTTT GGGAGGTTGAGGCAGGCGGA
TCACTTGAGCTC     5292
```

*Fig. 16B*

SERINE PROTEASE AND SERINE PROTEASE GENE

This application is a continuation of application Ser. No. 08/032,454, filed Mar. 17, 1993, now abandoned, which is a continuation of U.S. Ser. No. 07/735,187 filed Jul. 24, 1991, now abandoned, which is a continuation of U.S. Ser. No. 07/290,049, filed as PCT/JP88/00205, Feb. 26, 1988 published as WO88/06621, Sep. 7, 1988, now abandoned.

TECHNOLOGICAL FIELD

The present invention relates to the serine protease relating to inflammation and further relates to the serine protease having an ability to change the functions of lymphocyte, monocyte, NK cell and granulocyte, and also relates to the gene coding the serine protease.

Moreover, the present invention relates to a DNA sequence of a transcription controlling region which is necessary for cell-specific gene expression.

BACKGROUND TECHNOLOGY

Yosuke Aoki and others found a novel serine protease in erythroblast and granulocyte among myeloid cells and named the protease medullasin. They found that the function of medullasin is to activate NK cells and to cause inflammation (J. Biol. Chem. 253, 2026–2032 (1978); J. Clin. Invest. 69, 1223–1230 (1982)).

Moreover, Yosuke Aoki and others found and reported that medullasin also had the below described biological activities.

(1) Medullasin took part in controlling heme synthesis in an erythroblast and manifestation of pyridoxine reactive anemia.

(2) Medullasin took part in manifestation of anemia accompanied with chronic inflammation.

(3) Medullasin activity in a granulocyte increased when chronic inflammatory diseases became worse.

(4) When medullasin of physiological concentration was injected inside of an animal skin, an inflammation characterized by monocyte infiltration was caused and endothelial cells of fine vein were characteristically denatured.

(5) When human lymphocytes were treated with medullasin, their ability of DNA and RNA syntheses increased and their reactivity to various mitogens remarkably increased.

(6) When monocytes were treated with medullasin, their migration ability was obstructed whereas their superoxide productivity was increased.

(7) When granulocytes were treated with medullasin, their migration ability was increased.

(8) When human lymphocytes were treated with medullasin, their NK activity was remarkably increased but that was not through interferon production.

The total amino acid sequence of medullasin had not been determined, and only the supplier of medullasin was human bone marrow cell or human granulocyte. So the amount of medullasin available was limited.

The first purpose of the present invention is to clone the gene corresponding to medullasin by means of a genetic recombination method to clarify the sequence. It is thereby possible to clarify the gene coding medullasin or its precursor and at the same time to elucidate the amino acid sequence of the medullasin. The second purpose of the present invention is to enable us to synthesize medullasin by means of a chemical synthesis or a genetic recombination, and to obtain medullasin with high purity in large quantities.

Medullasin is contained in human myeloid cell or peripheral blood cells in large quantities. For example, about 10 μg of medullasin was found in 1 ml of human peripheral blood. This medullasin is hardly found in other tissues and cells but is expressed specifically in human blood cells, especially only in leukocytes and erythroblasts.

Therefore, it is expected that to clarify the expression mechanism of the medullasin gene is to elucidate the gene expression specific to human leukocytes or erythroblasts which have not been clarified before.

In general, cell-specific gene expression is controlled by not only factors (trans factors) such as proteins being specific to the cells and so on, but also by the gene sequences existing around and in the chromosomal genes. Therefore, it is thought that a DNA sequence of a transcription controlling region, which is necessary for gene expression being specific to leukocytes and erythroblasts among human blood cells, exists around or in the chromosomal gene of the above described serine protease, medullasin derived from human myeloid cells.

Therefore, the third purpose of the present invention is to propose a DNA sequence of a transcription controlling region necessary for the cell-specific gene expression.

SUMMARY OF THE INVENTION

The present invention is the biologically active serine protease which is a polypeptide having the amino acid sequence shown in FIG. 1 and the gene coding the serine protease.

Moreover, the present invention is a serine protease precursor in which a cleavagable peptide or a signal peptide is connected to the N-terminal of the mature serine protease exhibiting biological activity which is a polypeptide having whole or a part of the amino acid sequence shown in FIG. 1 and the gene coding the serine protease precursor.

Moreover, the present invention is the DNA sequence coding the transcription controlling region contained in the chromosomal gene of the serine protease of human myeloid cells.

BRIEF DESCRIPTION OF THE DRAWINGS

FIG. 1 represents an amino acid sequence of a polypeptide comprising serine a protease of the present invention.

FIG. 2 represents a DNA sequence containing a serine protease gene in accordance with the present invention.

FIG. 3 represents a sequence of 49 amino acid residues as described in Example 1.

FIG. 4 represents another DNA sequence containing a serine protease gene of the present invention.

FIG. 5 represents another form of amino acid sequence of a serine protease of the present invention.

FIG. 6 represents a serine protease precursor in accordance with the present invention.

FIG. 7 represents an example of a DNA sequence containing a serine protease precursor of the present invention.

FIG. 15 illustrates a DNA sequence encoding the transcription controlling region contained in a chromosomal gene of the serine protease derived from human myeloid cells or granulocytes.

FIGS. 16 (16-1 and 16-2) illustrates a chromosomal gene sequence containing a serine protease structural gene and its expression controlling region in accordance with the present invention.

THE BEST EMBODIMENT FOR PRACTICING THE INVENTION

Figure 8:
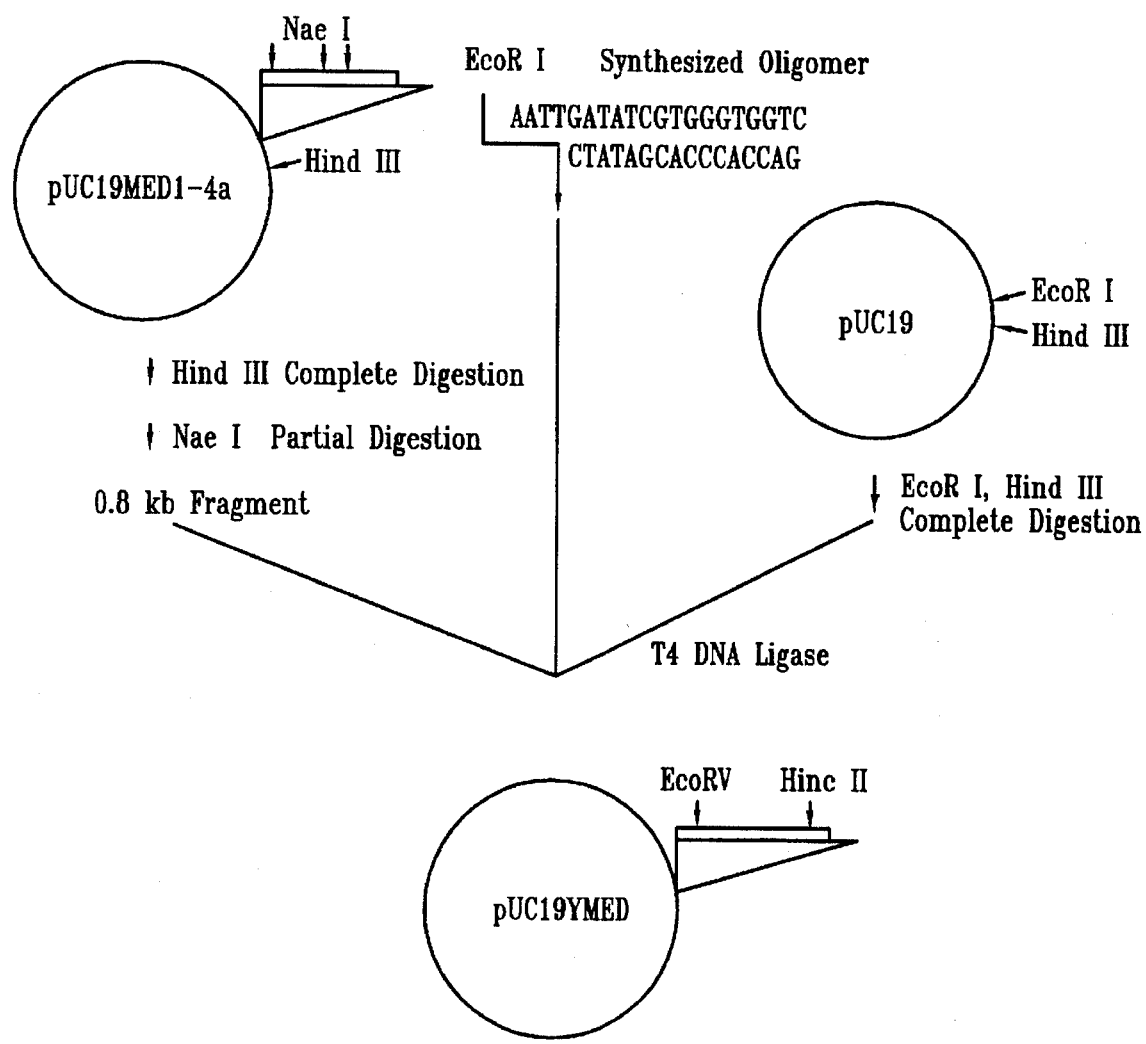
FIG. 8 is a diagram illustrating construction of the plasmid pUC19YMED.

The serine protease of the present invention is the polypeptide comprising the amino acid sequence of 238 residues as shown in FIG. 1 and as far as the same biological activity as this is substantially being kept, those polypeptides constituted by partial substitution, deletion and insertion in the above described amino acid sequence are also included in the serine protease of the present invention.

It is known that in general, a protease loses a part of the N-terminal and moreover a part of the C-terminal in some cases by the fact that the precursor protein synthesized through a messenger RNA from its gene receives processing and thereby becomes a mature protease.

The present invention expresses the serine protease of those embodiments that for example an amino acid sequence of C-terminal 19 residues in a polypeptide constituted of the amino acid sequence shown in FIG. 1 is deleted by receiving processing.

The serine protease gene of the present invention is the gene which codes the above described serine protease of the present invention and DNA sequence one containing the sequence shown in FIG. 2 is one of the representative examples.

The serine protease precursor of the present invention is the one in which a cleavagable peptide or signal peptide is connected to the N-terminal of the above described serine protease and one of the examples is shown in FIG. 6. The serine protease precursor shown in FIG. 6 is constituted of the amino acid sequence of 267 residues and it is the one in which 29 amino acid sequence containing a signal peptide are connected to the upper stream of the serine protease shown in FIG. 1.

The serine protease precursor gene of the present invention is the gene coding the serine protease precursor and the one containing the DNA sequence shown in FIG. 7 is its representative example.

As the whole amino acid sequence of the serine protease and its precursor of the present invention has been clarified by the present invention, it can be prepared by means of the known chemical synthesis, but also it can be prepared easily and in large quantities by means of a genetic recombination method.

For preparing the serine protease of the present invention by means of genetic recombination, at first, it is necessary to obtain the cDNA containing the serine protease gene. The cDNA can be preferably obtained by the following processes.

(1) Poly (A)$^+$ RNA is extracted from a cell producing the serine protease.

(2) cDNA is prepared by using the extracted Poly (A)$^+$ RNA as a template and reverse transcriptase, and a cDNA library containing various cDNAs is thereby obtained.

(3) A DNA probe hybridizing a target cDNA is chemically synthesized and the target cDNA is picked up by using this DNA probe from the cDNA library.

As the cell producing the serine protease used in the process (1), ML3 (cf. "Leukemia" edited by E. Henderson and F. Gunz, pp.119–139 (Grune & Strakton, New York, 1982)) which is the human APL (Acute Promyelocytic Leukemia) cell is preferably used because it continuously produces the serine protease.

The DNA probe used in the process (3) is obtained by chemically synthesizing and labelling a DNA oligomer which is a gene fragment corresponding to the amino acid sequence of the N terminal of the serine protease determined by the Edman degradation method.

A vector containing the serine protease gene is integrated in an appropriate expression vector to obtain a recombinant DNA. The target serine protease can be produced by introducing this recombinant DNA into such a host as *Escherichia coli, Bacillus subtilis*, a yeast or a cultured animal cell and by culturing the transformed cells obtained thereby. If such a eucaryotic cell as an animal cell is used as a host in this process, serine protease having a sugar chain can be obtained.

The above described gene manipulation can be carried out by the known method (T. Maniatis et al. "Molecular Cloning, A Laboratory Manual" (Cold Spring Harbor Lab. 1982)).

Moreover, when *Escherichia coli* is used as a host, the expression efficiency can be improved by using an expression vector containing a gene coding a chimera protein constituted by connecting such protein as a peptide derived from T7 phage, an anthranilic acid synthesizing enzyme (abbreviated as TrpE hereinafter) or β-galactosidase as a removable form to the upper stream of the serine protease of the present invention.

The serine protease can be easily isolated by digesting the chimera protein prepared above with an enzyme and so on.

Moreover, the present invention relates to a DNA sequence coding a transcription controlling region contained in a chromosomal gene of serine protease derived from a human myeloid cell.

The transcription controlling region of the present invention contains a promoter region and an enhancer and as the DNA sequence coding them, for example, the sequence shown in FIG. 15 or a sequence being equivalent thereto can be cited, but it is not restricted thereto. The word if of "equivalence" means here those ones in which the DNA bases are partly substituted with other DNA bases, are partly eliminated or other DNA bases are added thereto and which at the same time have the same functionality as that of the original DNA sequence.

The sequence shown in FIG. 15 corresponds to the 1st to 1,250th DNA sequence in the DNA sequence shown in FIG. 16. FIG. 16 shows a chromosomal gene sequence containing a structural gene of medullasin and its expression controlling region and this is the base sequence having been determined in a DNA fragment of about 6 kilobase having been cloned. In the sequence of FIG. 16, the whole length of the human medullasin gene is contained and the TATA sequence and CAAT sequence which are characteristic promoter components can be also confirmed. Compared with the base sequence of medullasin cDNA, it was clarified that the medullasin gene was constituted of 5 exons divided by 4 introns.

As the characteristic structures, 4 repeat sequences comprising 53 base pairs at the upper stream of the promoter structure and 10 direct repeat structures comprising 42 base pairs in the third intron can be observed. An AT rich structure capable of having a complicated second structure also exists in the third intron. A few sequences similar to the consensus sequence (GGCGGG, CCCGCC) bound by a SP1 protein which is a transcription controlling factor also exists near the promotor region.

The base sequence in a translation starting region of the medullasin gene well coincides with a base sequence which M. Kozack proposed as a necessary one for starting an effective translation. It is estimated that this is one of the reasons why the medullasin protein exists in relatively large quantities such as about 10 µg per 1 ml of human peripheral blood.

Moreover, as shown in the examples, the present inventors found that by examining the quantity of poly(A)$^+$ RNA in cells by means of the Northern blotting analysis, poly(A)$^+$ RNA of medullasin was expressed in large quantities in ML3 cells (described above) which are human acute promyelocyte leukemia cells, but very little expressed, for example, in diploid fibroblasts derived from a human fetal pulmonary tissue or in cell strain MIAPaCa-2 cells derived from a human pancreatic malignant epithelial tumor.

It can be said from these results that the transcription controlling region is a sequence for a specific gene expression in human hemocyte cells, especially erythroblasts and granulocytes.

The present invention will be hereinafter more concretely explained by the following examples. In the examples, the word of mature serine protease was used not to mix up the serine protease of the present invention with a serine protease precursor.

EXAMPLE 1

Preparation of serine protease cDNA and determination of the serine sequence (A) Synthesis of DNA probe 225 µg of purified medullasin obtained by means of the method of Aoki et al. (J. Biol. Chem. 253, 2026–2032 (1978)) were analyzed by using a gas phase automatic peptide sequencer type 470A (manufactured by Applied Biosystems Co., Ltd.). The sequence of 49 amino acid residues from the N terminal was determined as shown in FIG. 3 by analyzing the obtained fraction by means of high-performance liquid chromatography. Some uncertainty was left by means of this analytical method in analyzing the amino acid residues being put in parentheses.

Among the above described 49 amino acid residues, a part of the amino acid sequence $^{12}$Trp-Pro-Phe-Met-$^{16}$Val, in which the degree of degeneration of DNA to be coded was little, was selected and 8 kinds of DNA oligomers of 14 base length excluding a base of 5' terminal (this is the third base coding Val) having a complementary DNA base sequence being complementary to the DNA base sequences coding this part of the amino acid sequence were chemically synthesized by means of a known method. (It was based on the fact that there are 4 codons coding proline and 2 codons coding phenylalanine.) The base sequences of these 8 kinds of DNA oligomers were described as follows. 5' hydroxyl groups in the equivalent mixture of 8 kinds of DNA oligomers were labelled by phosphorylation with T4 polynucleotide kinase and γ $^{32}$U.C.-ATP to obtain a DNA probe.

5' ACCATAAAAGGCCA 3'

5' ACCATAAACGGCCA 3'

5' ACCATAAAGGGCCA 3'

5' ACCATAAATGGCCA 3'

5' ACCATGAAAGGCCA 3'

5' ACCATGAACGGCCA 3'

5' ACCATGAAGGGCCA 3'

5' ACCATGAATGGCCA 3'

(B) Preparation of Poly (A)$^+$ RNA

A cell line ML3 was cultured in RPMI 1640 medium containing 10% fetal calf serum at 37° C. in 5% density carbon dioxide. When the cell reached about 1×10$^6$ cells/ml, cycloheximide was added to the medium to make its concentration to be 30 µg/ml and the culture was continued for more 5 hours. 30 ml of a solution comprising 6M guanidine thiocyanate, 2% sarcosyl, 50 mM Tris hydrochloride (pH 7.6), 10 mM EDTA and 1% β-mercaptoethanol was added to the cells obtained above (about 1.4×10$^9$ cells) and a viscous solution obtained was passed through 18G injection needle five times.

This cell homogenate was placed in 5.7M cesium chloride solution (containing 100 mM EDTA) whose volume was one third of the homogenate and centrifuged at 35000 rpm at 25° C. overnight. RNA precipitated on the bottom of the centrifuge tube was dissolved in a small amount of water and precipitated with ethanol after phenol treatment to obtain 640 µg of total RNA.

This total RNA was fractionated in the usual way by means of oligo dT cellulose column chromatography to selectively obtain 86 µg of poly(A)$^+$RNA.

(C) Preparation of cDNA

Using 5 µg of poly(A)$^+$RNA obtained in the preceding paragraph, 640 ng of double strand cDNA was synthesized by the method of Gubler and Hoffman (Gene, 25, 263 (1983)) by utilizing a cDNA synthesizing kit (manufactured by Amersham) according to its protocol. Then, EcoRI linkers were connected to both terminals by using the cDNA cloning system (manufactured by Amersham) and the reaction mixture was digested with EcoRI. 434 ng of double strand cDNA having EcoRI-attached terminals on its both ends were thereafter obtained by means of gel filtration column. 86 ng of this double strand cDNA was ligated to 1 µg of λgt10 arms by using T4 ligase and the reaction was added to the λ phage-packaging-extract and a mixture of recombinant phages (Materials of cDNA cloning system manufactured by Amersham Co., Ltd. and its recipe were used) was obtained. 9.6×10$^4$ pfu (plaque-forming unit) of recombinant phages (cDNA library) were obtained by using *Escherichia coli* NM514 as a host.

(D) Isolation of serine protease cDNA clone

About 25,000 recombinant phages obtained above were seeded one *Escherichia coli* NM514 as a host in one Petri dish whose diameter was 145 mm containing LB medium and 4 master plates were thereby prepared. After the phage was transferred on a nitrocellulose filter, phage DNA was fixed on the filter by means of alkaline denaturation. The procedure of R. Davis et al. ("DNA Cloning" edited by D. M. Glover, Vol. I, p.49–78 (IRL Press) (1985)) was applied correspondingly to these procedures.

The filters where phage DNA was fixed by the above described procedure were screened by means of hybridization using the DNA probe prepared in paragraph (A). The hybridization was carried out at 35° C. and washing was carried out at 35° C., too. The procedure of T. Maniatis ("Molecular Cloning, A Laboratory Manual" (Cold Spring Harbor Lab. (1982)) was applied correspondingly to these procedures. 7 positive of clones detected by means of autoradiography were obtained hybridization.

(E) Determination of base sequence of serine protease cDNA

Phage DNA of MED1-4a which was one of the positive clones obtained in the preceding paragraph was extracted and cut by using EcoRI to obtain about 800 base pairs of DNA fragments. This fragment was inserted into EcoRI site of a cloning vector pUC19 (manufactured by Takara Shuzo Co., Ltd.), and of a phage M13mP19-RFDNA (manufactured by Takara Shuzo Co., Ltd.) for sequencing. Sequence analysis was carried out by means of the dideoxy method using deoxy-7-deaza guanine triphosphate. For analyzing the central parts, primers corresponding to the surrounding parts whose sequences had been already determined were successively synthesized and the sequence analyses were carried out by means of the dideoxy method. DNA sequence shown in FIG. 4 was thus determined. In the DNA sequence shown in FIG. 4, the upper stream including the 7th C and the lower stream including the 807th G were derived from EcoRI linker GGAATTCC used for cloning to λgt10 vector. Therefore, DNA base sequence from 8th to 806th in the figure was cDNA derived from poly(A)$^+$RNA. The longest open leading frame (the protein-coding region) was searched and it was found that the translated coding frame of the DNA sequence from 8th to 718th in the figure was the longest and a termination codon TGA succeeded from the 719th one. The translated amino acid sequence corresponding to the DNA sequence from 8th to 718th was shown in FIG. 5. The amino acid sequence from the 1st to the 48th in the figure was completely identical with the amino acid sequence from the 2nd to the 49th of the purified medullasin shown in FIG. 3. It was concluded from this result that the DNA sequence from the 8th to the 718th in the DNA sequence shown in FIG. 4 constituted cDNA which codes the part of the serine protease of the present invention and this cDNA part was shown in FIG. 2. The cDNA lacked the part coding isoleucine (Ile) which was the N terminal amino acid of purified medullasin shown in FIG. 3, but because it was clear from the above described analysis of the amino acid sequence of the purified medullasin that Ile was the N terminal of medullasin. It can be concluded that whole cDNA sequence coding the serine protease of the present invention is the one where ATT, ATC or ATA coding Ile is added to the 5' terminal side of the base sequence shown in FIG. 2. The amino acid sequence corresponding to this whole cDNA, namely, the amino acid sequence of the serine protease of the present invention was shown in FIG. 1.

EXAMPLE 2

Preparation of a full length cDNA of serine protease and determination of the base sequence Five positive clones having longer serine protease cDNA than 800 base pairs of the clone MED1-4a obtained in Example 1 were isolated by using the partial cDNA obtained in Example 1 as a probe from about one million plaques of the λgt10 cDNA library which was newly synthesized by the similar method as that of Example 1, paragraph (C) using 5 μg of ML3 cell poly(A)$^+$RNA prepared in the similar way as Example 1, paragraph (B). The base sequence of the region coding N-terminals of serine protease of clone MED10 and MED13 among the five positive clones was determined by the same method as that of Example 1, paragraph (E). It was found that MED13 and MED10 contained more 89 and 128 base pairs upper stream than that of MED1-4a. Therefore, the sequence of cDNA of serine protease precursor can be as shown in FIG. 7. It was estimated from these DNA sequences that the serine protease precursor comprised 267 amino acid and 29 more amino acids were connected to the upper stream of isoleucine located at the N-terminal of a mature serine protease (FIG. 6). Among the leader peptide comprising these 29 amino acids, 27 amino acids of the N-terminal side comprised 17 hydrophobic amino acid (9 leucines, 5 alanines, 1 phenylalanine, 1 valine and 1 proline) and had the most recognizable sequence with a signal peptidase comprising alanin-leucine-alanine on its C-terminal side. Therefore, they were thought to be a signal peptide. Moreover, it was estimated that a peptide comprising 2 amino acids, serine-glutamic acid, located on the lower stream of this leader peptide is an activation peptide.

EXAMPLE 3

Preparation of a expression vector pETMED expressing serine protase in *Escherichia coli* and expression of T7-serine protease chimera protein (A) Preparation of a mature serine protease cDNA vector pUC19YMED:

At first the EcoRI fragment of cDNA obtained by Example 1 shown in FIG. 4 was inserted in EcoRI site of a cloning vector pUC19 and a plasmid DNA pUC19MED1-4a was selected by confirming the inserting direction where the down stream part of the DNA shown in FIG. 4 was close to BamHI site of pUC19.

This vector pUC9MED1-4a was completely digested with HindIII and then partially digested with NaeI. An 810 base pair fragment of the serine protease cDNA was thereby obtained. A vector pUC19YMED having a mature serine protease cDNA was prepared by inserting this DNA fragment and a synthesized oligomer coding the N-terminal of the mature serine protease between EcoRI site and HindIII site of pUC19 by using T4DNA ligase (FIG. 8).

Figure 9:
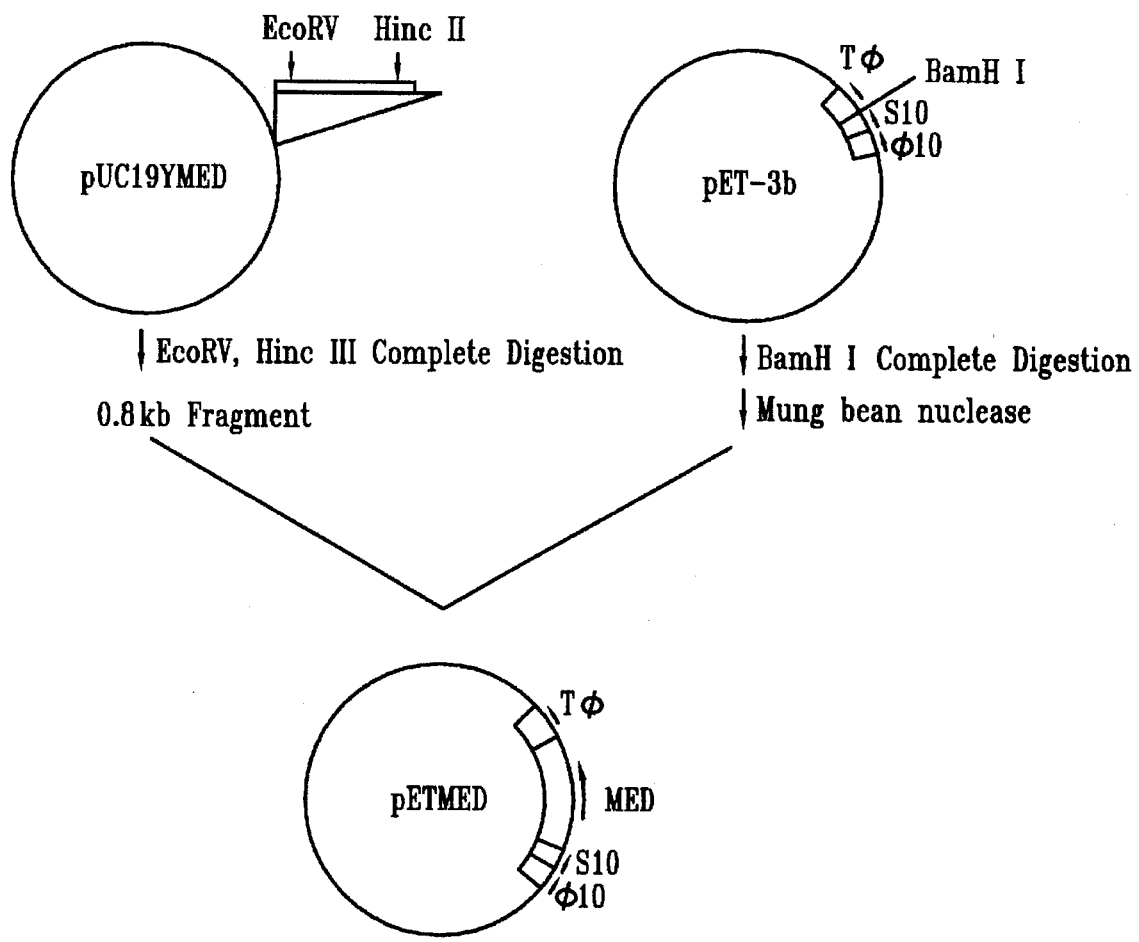
FIG. 9 is a diagram illustrating construction of the plasmid pETMED.

(B) Preparation of pETMED:

pET-36 distributed by Dr. F. William Studier (Biology Department, Brookhaven National Laboratory, Upton, N.Y.) was completely digested with BamHI located on the lower stream of T7 promoter and thereafter made to a blunt end by Mung bean nuclease treatment. Then, pUC19YMED of the paragraph (A) was completely digested with ECoRV and HincII and about 0.8 Kb of DNA fragments comprising a maturation serine protease cDNA were isolated. A vector pETMED expressing serine protease *Escherichia coli* was prepared by connecting these two DNA fragments by using T4DNA ligase (FIG. 9). From this vector, a chimera protein having 250 amino acids where a peptide comprising 11 amino acids (Met-Ala-Ser-Met-Thr-Gly-Gly-Gln-Gln-Met-Gly) derived from T7 phage and a mature sertne protease comprising 238 amino acids were connected each other between which arginine was placed, was prepared. The mature serine protease can be isolated by digesting partly this chimera protein with trypsin.

(C) Expression of T7-serine protease chimera protein by using pETMED:

At first, pETMED prepared in the paragraph (B) was introduced into *Escherichia coli* HMS174 (J. L. Campbell et al., Proc. Natl. Acad., Sci., U.S.A. 75, 2276–2280 (1978)). This recombinant was cultured at 37° C. overnight on 5 ml of LB medium (T. Maniatis et al., "Molecular Cloning", p.440 (1982)) containing 100 μg/ml of ampicillin and 0.4% (w/v) of maltose and then 0.1 ml of this was transferred on a NZCYM medium (T. Maniatis et al., "Molecular Cloning", p.440 (1982)) containing 100 μg/ml of ampicillin and 0.4% (w/v) of maltose. This was cultured at 37° C. until the absorbance at 600 nm became to 0.3, thereafter infected with phage CE6 (F. W. Studier et al., J. Mol. Biol., 189, 113–130 (1986)) whose quantity was 5 to 10 times of *Escherichia coli* and cultured at 37° C. for 3 hours. By analysing the whole protein of the bacteria obtained above by means of SDS polyacrylamide gel electrophoresis, a protein whose molecular weight was about 29,000 was observed and which was not observed in bacteria where a control pET-36 (above described) was introduced. It was confirmed by means of Western blotting using an anti-medullasine antibody that this protein was T7 serine protease chimera protein.

EXAMPLE 4

Figure 10:
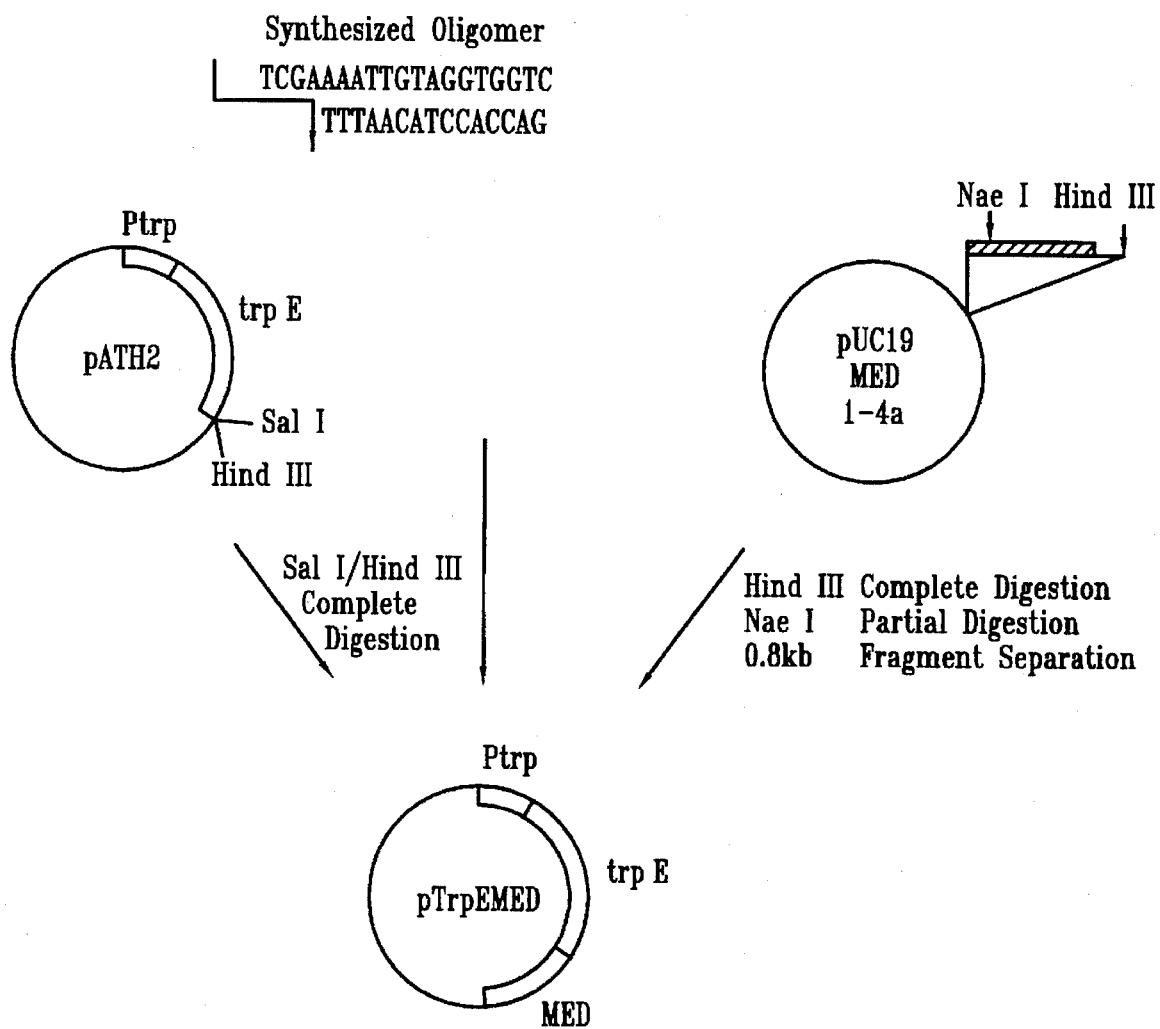
FIG. 10 is a diagram illustrating construction of the plasmid pTrpEMED.

Preparation of a vector pATH2MED expressing TrpE-serine protease and expression of TrpE-serine protease chimera protein (A) Preparation of a vector pATH2MED expressing TrpE-serine protease:

A DNA fragment of about 800 base pairs containing a serine protease partial gene was isolated by digesting completely pUC19MED1-4a in Example 1 with HindIII and thereafter digesting partially with NaeI. This fragment and a synthesized oligomer coding the N-terminal side of serine protease were inserted between SalI and HindIII sites of a vector pATH2 for expressing TrpE chimera protein (C. L. Dieckman and A. Tzagoloff, J. Biol. Chem. 260, 1513–1520 (1985)) by using T4DNA ligase and thus a vector pATH2MED expressing a chimera protein of TrpE-serine protease was prepared (FIG. 10).

A chimera protein comprising 570 amino acids in which a peptide comprising 331 amino acids derived from TrpE and a maturation serine protease comprising 238 amino acids were connected each other between which lysine was placed was prepared from this vector. The mature serine protease can be isolated by digesting partially this chimera protein with an endoprotease lysC.

(B) Expressing TrpE-serine protease chimera protein by using pATH2MED:

*Escherichia coli* HB101 transformed with pATH2MED was cultured at 30! C for 7 hours in LB medium containing 100 μg/ml of ampicillin (T. Maniatis et al., "Molecular Cloning", p.440 (1982)). 4 ml of this culture was transferred to 40 ml of M9 medium (T. Maniatis et al. "Molecular Cloning", p.68 (1982)) containing magnesium sulfate, thiamin hydrochloride, glucose and ampicillin with the concentration of 1 mM, 1 μg/ml, 1% (w/v) and 100 μg/ml respectively, cultured at 25° C. overnight and further cultured for 8 hours after adding 0.8 ml of glucose, 0.16 ml of 14% (w/v) ammonium hydroxide and 40 μl of 10 mg/ml indoleacrylic acid.

By analyzing the whole protein of the bacteria by means of SDS polyacrylamide gel electrophoresis, a chimera protein of TrpE-serine protease whose molecular weight was about 61,000 and which was not observed in HB101 where a control pATH2 was introduced, was confirmed. It was confirmed by means of Western blotting using an anti-medullasin antibody that this protein was a chimera protein of the serine protease.

EXAMPLE 5

Figure 11:
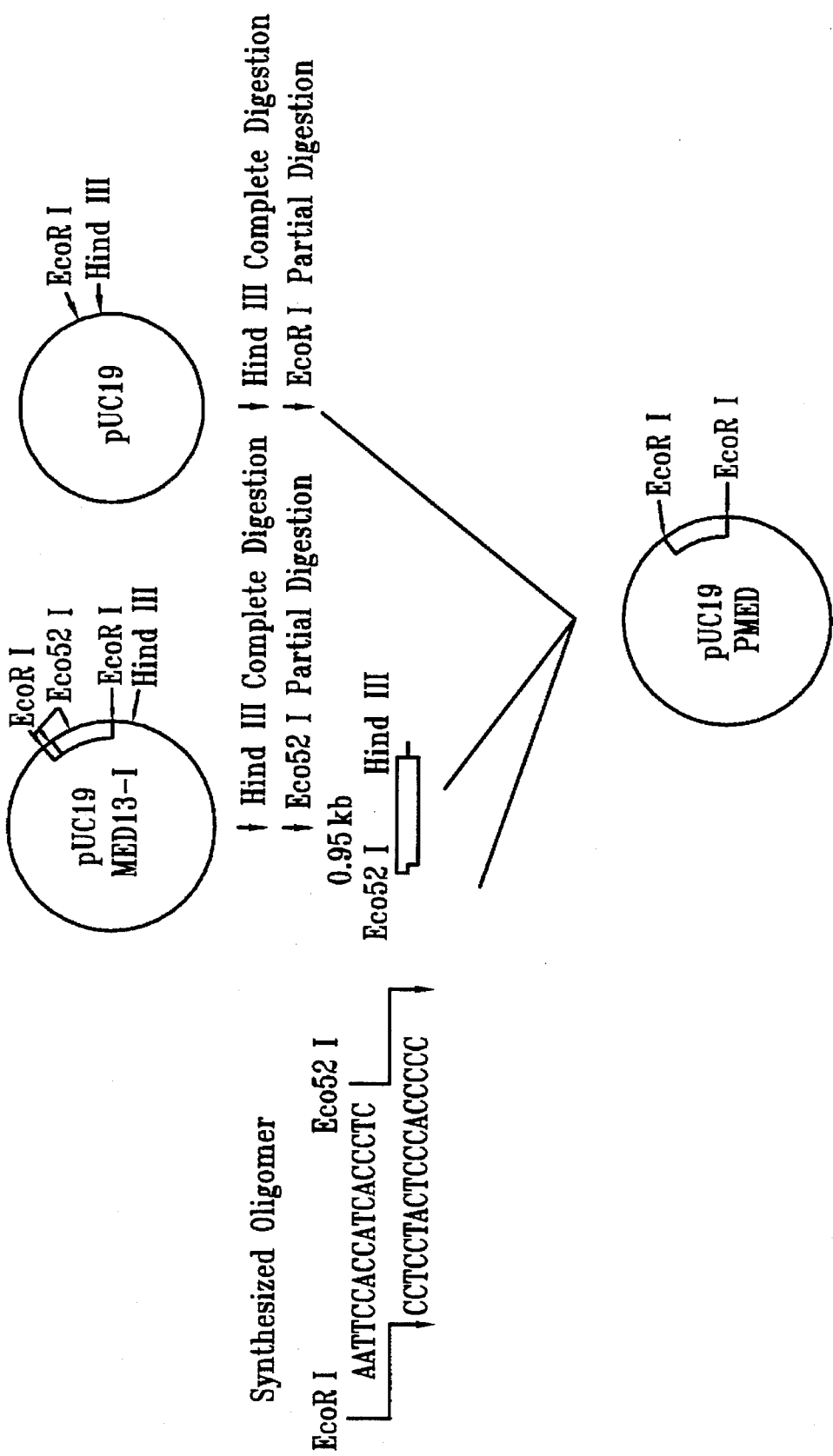
FIG. 11 is a diagram illustrating construction of the plasmid pUC19pMED.

Preparation of a serine protease yeast vector pATMED and Expression of a serine protease (A) Preparation of serine protease precursor cDNA vector pUC19PMED:

A DNA fragment of about 950 base pairs was separated by digesting completely pUC19MED13 in Example 3 with HindIII and thereafter digesting partially with Eco521. A vector pUC19PMED having a sertne protease precursor cDNA was prepared by inserting this fragment and synthesized oligomers coding the N-terminal of serine protease precursor between EcoRI site and HindIII site of pUC19 by using T4DNA ligase (FIG. 11).

Figure 12:
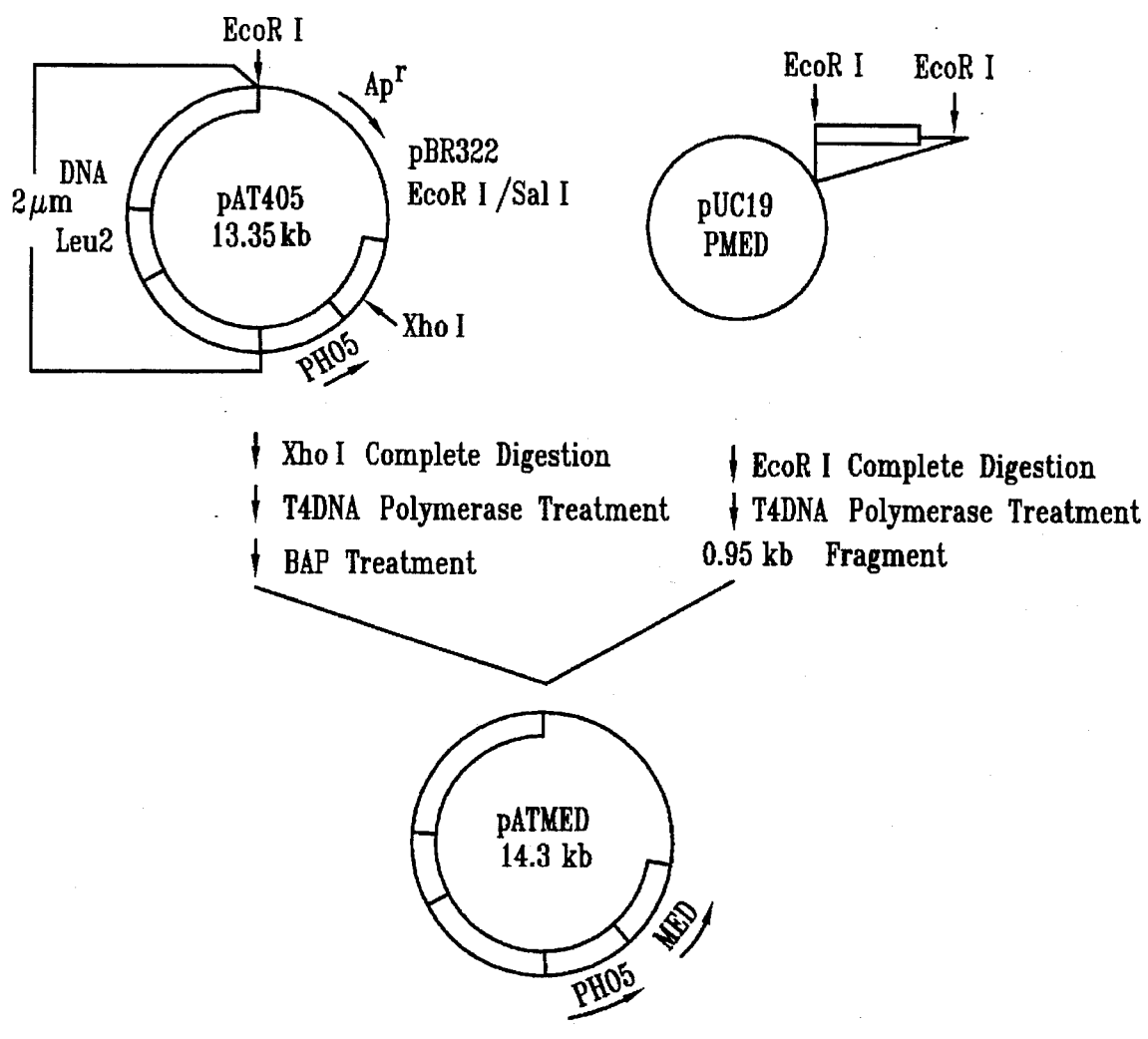
FIG. 12 is a diagram illustrating construction of the plasmid pATMED.

(B) Preparation of pATMED:

At first, a vector pAT405 having PH05 (inhibitory acidic phosphatase) promoter of a yeast distributed from Dr. Tobe of Hiroshima University was completely digested with XhoI and thereafter made to a blunt end by T4DNA polymerase treatment. Phosphoric acid at of the terminal was removed by *Escherichia coli* alkaline phosphatase treatment. Then, pUC19PMED in the paragraph (A) was completely digested with EcoRI and thereafter made to blunt end by T4DNA polymerase treatment. A DNA fragment of about 950 base pairs containing the serine protease precursor cDNA was thereafter isolated. A vector pATMED expressing a serine protease in yeast was prepared by connecting these 2 DNA fragments by using T4DNA ligase (FIG. 12).

(C) Expressing a serine protease by using pATMED:

pATMED-introduced yeast DC5 (distributed by Dr. Tobe of Hiroshima University) was cultured at 30° C. overnight in 5 ml of Yeast Nitrogen Base medium (manufactured by Difco) containing histidine and glucose with the concentration of 0.1 mg/ml and 2% (w/v) respectively. 2.5 ml of the culture was transferred to 50 ml of the same medium and cultured further at 30° C. overnight. The bacteria were collected, washed once with 50 ml of water, suspended in 50 ml of a phosphorus-free medium (using KCl instead of KH$_2$PO$_4$ of Yeast Minimal Medium (R. L. Rodriguez and R. C. Trait "Recombinant DNA techniques" p151 (1983)) and cultivated at 30° C. for a day and half. One ml of the cultured supernatant was concentrated by lyophilization and then analysed by SDS polyacrylamide gel electrophoresis. A protein whose molecular weight was about 32,000 and which was not observed in the cultured supernatant of DC5 in which a control pAT405 was introduced, was thereby detected. It was confirmed by means of Western blotting using an anti-serine protease antibody that this protein was the serine protease.

EXAMPLE 6

Figure 13:
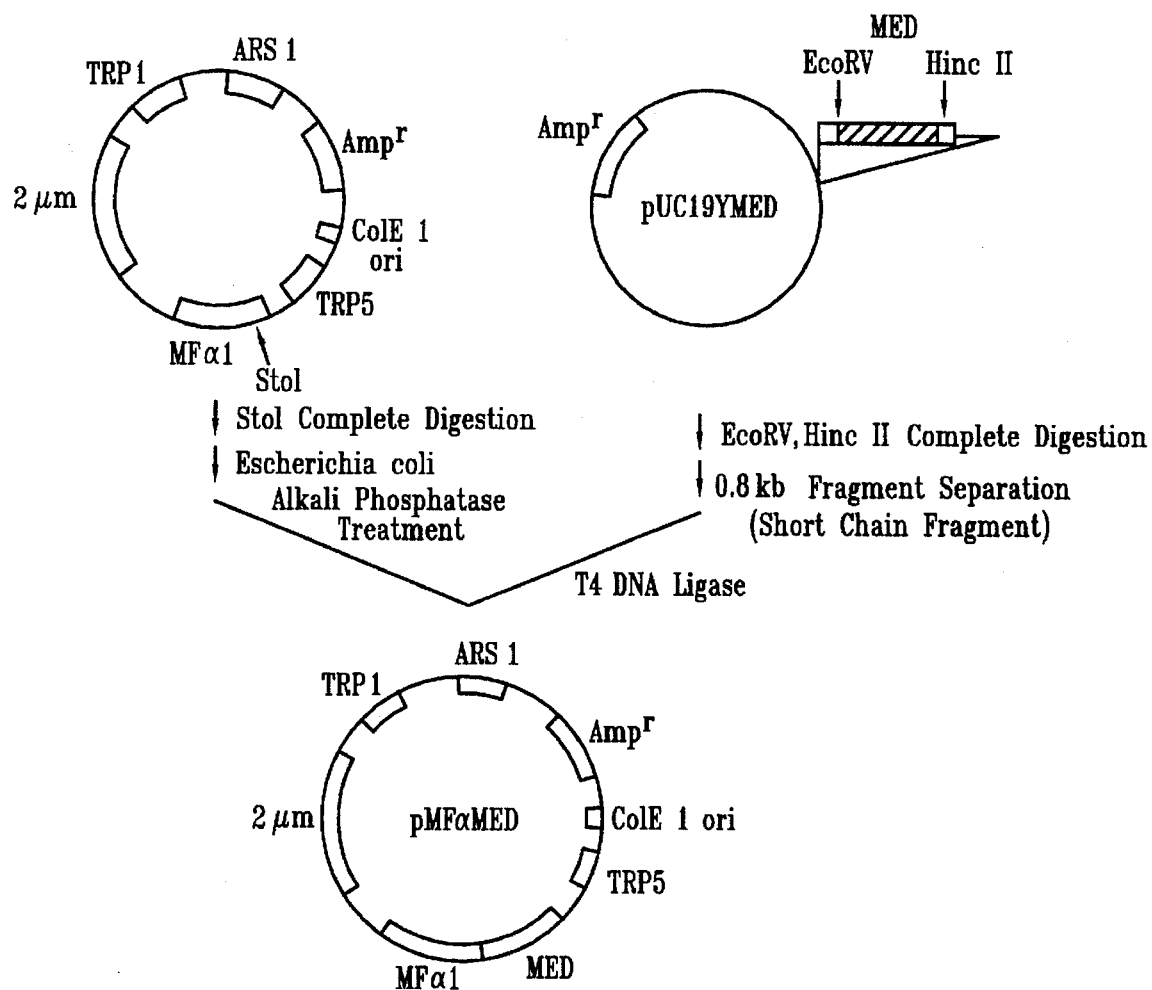
FIG. 13 is a diagram illustrating construction of the plasmid pMFαMED.

Preparation of a vector pMFαMED expressing a yeast of serine protease and expression in a yeast (A) Preparation of a vector pMFαMED expressing a yeast of serine protease:

pUC19YMED in Example 4 paragraph (A) was completely digested with EcoRI and HincII and a DNA fragment of about 800 base pairs comprising a maturation serine protease cDNA was isolated. Then, a promoter of α-factor which was a mating pheromone of yeast and a vector pMFα8 (A. Miyajima et al., Gene, 37, 155 (1985)) having a leader sequence were completely digested with StuI and thereafter dephosphorylated by means of *Escherichia coli* alkaline phosphatase treatment. A vector pSRαMED for expressing the serine protease in yeast was prepared by connecting these two DNA fragments by using T4DNA ligase (FIG. 13).

(B) Transformation of a yeast 20B12 with pSRαMED:

10 μg of pSRαMED in paragraph (A) were introduced into about 1×10$^7$ cells of yeast 20B12 (distributed from Dr. Tobe of Hiroshima University) by means of alkaline metal treatment (A. Kimura et al., J. Bacteriol., 153, 163(1983)). The transformed cell thus obtained was cultured at 30° C. overnight in 5 ml of a Yeast Nitrogen Base medium (manufactured by Difco) containing glucose with a concentration of 2% (w/v). 1 ml of the culture was then transferred to 10 ml of the same medium and cultivated for more 24 hours. 1 ml of the cultured supernatant was concentrated by lyophilization and then analyzed by means of Western blotting using an anti-serine protease (medullasin) antibody. A protein whose molecular weight was about 32,000 and which was not observed in the cultured supernatant of 20B12 in which a control pMFα8 was introduced, was thereby detected.

EXAMPLE 7

Preparation of a vector pSαMED expressing the serine protease in animal cell and expression in animal cell.

Figure 14:
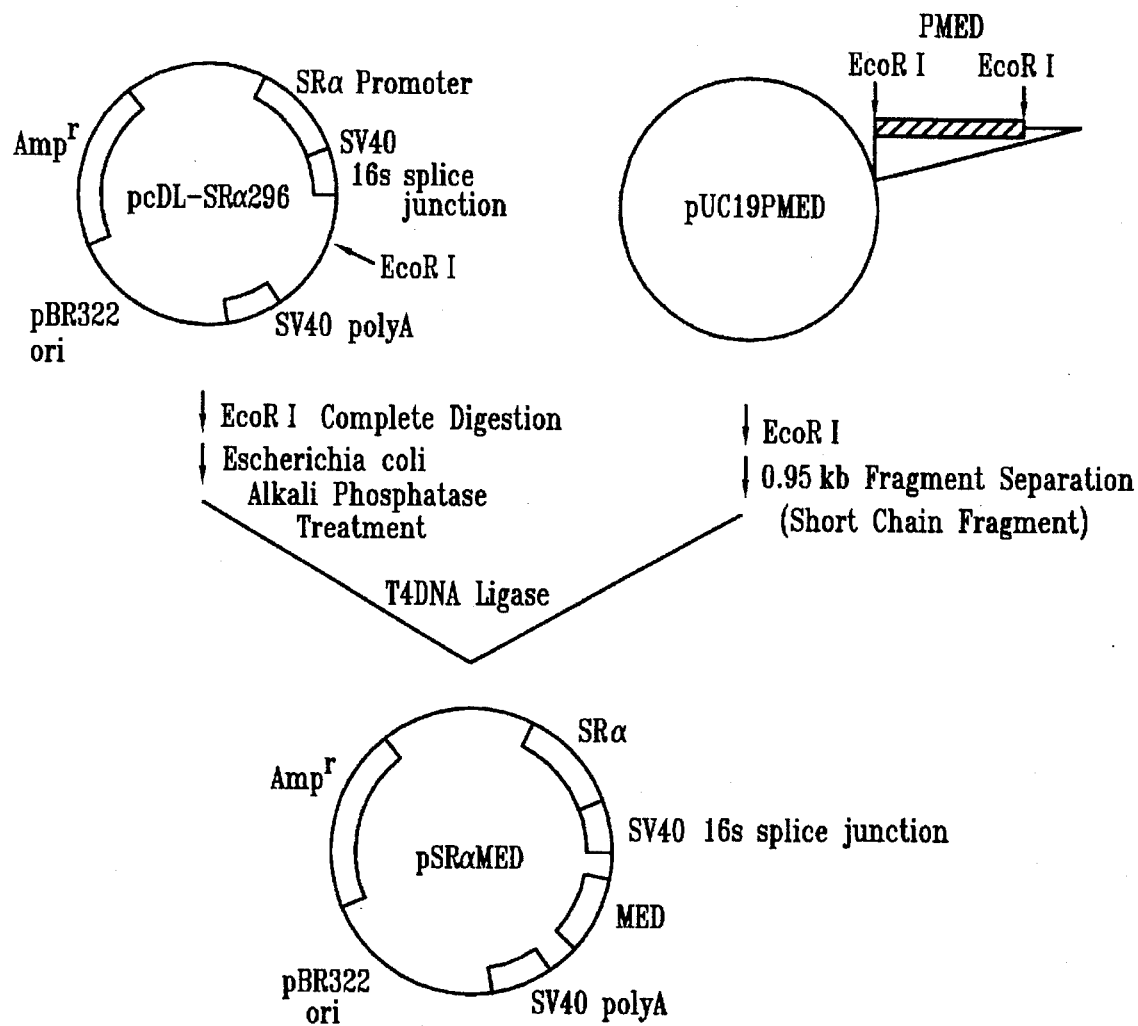
FIG. 14 is a diagram illustrating construction of the plasmid pSRαMED.

(A) Preparation of a vector pSRαMED expressing the serine protease in animal cell:

pUC19PMED in Example 6, paragraph (A) was completely digested with EcoRI and a DNA fragment of about 950 base pairs containing a serine protease precursor cDNA was separated. This was connected with a vector obtained by digesting pcDLSRα296 (obtained from Dr. Takebe, DNAX) completely with EcoRI and dephosphorylating it by means of *Escherichia coli* alkaline phosphatase treatment by using T4DNA ligase and a vector pSRαMED expressing the serine protease in animal cell was thereby prepared (FIG. 14).

(B) Transformation of Cos-1 cell with pSRαMED:

10 μg pSRαMED in the paragraph (A) were introduced into about 2×10$^6$ pieces of Cos-1 cells derived from a monkey kidney (Y. Gluzman, Cell, 23, 175 (1981)) by means of calcium phosphate method (F. L. Graham et al., Virology, 54., 536). The cells were collected after 5 days and proteins of whole cells were analysed by means of Western blotting using an anti-serine protease (medullasin) antibody. A protein whose molecular weight was about 30,000 and which was not observed in COS-1 cells in which a vector was not introduced, was detected. Activity of the said enzyme was measured by the reported method (L. Visser et al., Biochem. Biophys. Acta, 268, 257 (1972)) using p-nitrophenyl N-tert-butyloxycarbonyl-L-alaninate which was a general substrate of elastases as the substrate. The soluble fraction obtained by breaking the cells by freeze-thaw and by centrifuging at 12,000 g for 30 minutes showed an activity increasing the absorbance at 347.5 nm by 0.1 per about 1×10$^6$ cells in comparison with a control.

EXAMPLE 8

Southern hybridization of chromosome DNA:

Before cloning of the human medullasin gene, at first, Southern hybridization was carried out. Each 10 μg of chromosome DNA derived from a human tonsil (The method of preparation was based on the method described in P. Chambon et al., Eur. J. Biochem, 36, p.32–38 (1973)) was cut with restriction enzyme EcoRI, BamHI ir PstI, fractionated using an agarose gel. Southern hybridization was carried out using medullasin cDNA as a probe after the Southern blotting. It was clarified from the result that only about 6 kb of fragment from EcoRI, digestion hybridized with the human medullasin cDNA probe and that only one kind of the human medullasin gene existed in the chromosome and it was contained in the 6 kb fragment of EcoRI.

The medullasin cDNA probe used here was prepared by labelling the cDNA (the EcoRI inserted fragment, about 800 bp) described in K. Okano et al., J. Biochem. 102, p.13–16 (1987) with $^{32}$p by nick translation.

EXAMPLE 9

Cloning of the human medullasin gene:

About 100 μg of human chromosome DNA was cut with EcoRI and the DNA of about 6 kb length was recovered from agarose gel electrophorests. The recovered DNA was ligated with EcoRI digested arm-DNA of a vector λgtWES·λβ derived from a λ phage (obtained from BRL) as a vector (ligase reaction) and a gene library was prepared by means of in vitro packaging (The in vitro packaging kit was obtained from Takara Shuzo Co., Ltd.). A gene library of 5×10$^4$ pfu could be prepared from 0.5 μg of the recovered DNA and 0.1 μg of the vector DNA. This gene library was screened by means of an ordinary plaque hybridization (T. Maniatis et al., "Molecular Cloning: A Laboratory Manual (abbreviated as a book A hereinafter)" p.312–318 (Cold Spring Harbor Laboratory (1982)) by using a nick translated medullasin cDNA as a probe (The nick translation kit was obtained from Takara Shuzo, Co., Ltd.) As the result, 3 pieces of positive clones were obtained. One of them was named as λMED-2.

EXAMPLE 10

Determination of the base sequence of λMED-2:

The EcoRI inserted fragment of λMED-2 was subcloned in a sequencing vector pUC18 DNA or pUC19 DNA (obtained from Takara Shuzo Co., Ltd.) and appropriate deletion variants was obtained by using a kilo-deletion kit (obtained from Takara Shuzo Co., Ltd.) Each base sequence was determined by means of the dideoxy sequencing method using a 7-DEAZA sequence kit (obtained from Takara Shuzo Co., Ltd). The result was shown in FIG. 1. Namely, among inserted fragments of cloned λMED-2, 5292 base sequence was determined and shown in FIG. 1. CAAT box, TATA box and poly A signal were surrounded with small boxes and the regions coding proteins in medullasin mRNA were also surrounded with squares. Repeating sequences existing in the upper stream of a promoter and in the third intron were indicated with arrow-marked underlines. However, it is possible that the position of the 5' terminal of the mRNA a may be different from the actual position by some several bases.

EXAMPLE 11

ML3 cells, normal diploid fibroblasts derived from a human fetal lung and MIAPaCa-2 cells were cultured in 5% carbon dioxide gas at 32° C. in a RPMI1640 medium containing a fetal calf serum (ML3), an Eagle's MEM medium containing fetal calf serum (normal diploid fibroblasts derived from a human fetal lung) or a Dalbecco's MEM medium containing 10% fetal calf serum and 2.5% equine serum (MIAPaCa-2 cells) respectively. 16 ml of a solution containing 6M guanidinethiocyanate, 2% sarcosil, 50 mM (U.C.) Tris chloride (pH=7.6), 10 mM EDTA, 10% β-mercaptoethanol were added in 2 to 5×10$^6$ cells and the viscous solution obtained was passed through a 19G injection needle five times. This cell homogenate was placed on 18 ml of 5.7M secium chloride solution containing 100 mM EDTA and centrifuged at 35,000 rpm at 25!C overnight. RNA precipitated on the bottom of the centrifuge tube was dissolved in a buffer solution and treated with phenol. Whole RNA was thereafter obtained by precipitating with ethanol.

These procedures were carried out in accordance with the method described on page 196 of the book A. The quantity of the whole RNA thus obtained was 200–600 μg. These whole RNA were treated in an oligo dT column by the method described on page 192–198 of the book A to obtain a polyA(+)RNA. Each 10 μg of these polyA(+)RNA was fractionated with formaldehyde agarose gel electrophoresis and then transferred to a nitrocellulose filter. These procedures were carried out in accordance with the method described on page 202–203 of the book A.

The nitrocellulose filter thus obtained was analysed by means of the Northern hybridization, which was carried out in accordance with the Southern hybridization described in page 387–389 of the said book. As the probe, cDNA of serine protease (medullasin) described in the literature, K. Okano, et al., J. Biochem. 102, p.13–16 (1987) being labelled with [$\alpha^{32}P$] dCTP by means of the translation (described on page 109–112 of the said book A) and whose specific activity was about. $1 \times 10^8$ cpm/μg, was used. The concentration of the probe was $2 \times 10^6$ cpm/ml and the hybridization was carried out with the condition of 50% formamide at 42° C. By exposing a XAR-5 film of Kodak at 70° C. overnight in the presence of an intensifying screen, a clear band was observed on the position of about 1,000 base length on the lane of RNA from ML3 cells. However, no detectable band was observed on the lanes where RNA obtained from other cells was electrophorased.

Industrial Application

Serine protease of the present invention takes part in manifestation of inflammation and it is therefore important to develop an anti-inflammatory drug. Moreover, it has an activity to change the functions of lymphocyte, monocyte, NK cell and granulocyte and therefore it is very useful in the medical care field.

Moreover, serine protease of the present invention can be useful medical supplies. For example, because serine protease of the present invention has a thrombus dissolving action, it is possible to use it as a thrombus dissolving agent for DIC (disseminated intravascular coagulation). Papain which is a protease derived from a plant may Be used formerly in some cases for a medical treatment of DIC, it is anxious about that dangerous side effects may occur because the action is too strong and allergic reaction due to the antigenesity is induced. In this respect, there is a merit that serine protease of the present invention can be used safely because it is an enzyme derived from human being. Moreover, as another example of applications for medical supplies, for medical treatments of external injuries, it is possible to use the serine protease as a medicine for external application for removing and modifying granuloma-like rised tissues or old skin tissues. In this case, serine protease of the present invention can be safely used as it is derived from human being.

Moreover, the DNA sequence of the present invention of the transcription controlling region being necessary for the cell specific gene expression is useful for carrying out specifically the expression of foreign gene on a leukocyte or an erythroblast cell, above all, cultured cell strains derived from them.

We claim:

1. A composition comprising a nucleic acid molecule coding an amino acid sequence as set forth in FIG. 1.

2. A serine protease produced by culturing a transformed cell with an expression vector containing a serine protease gene encoding an amino acid sequence as set forth in FIG. 1.

3. A serine protease according to claim 2 wherein the expression vector contains the sequence as set forth in FIG. 2.

4. An isolated serine protease precursor having a serine protease signal peptide operably linked to an N-terminus of a serine protease produced by culturing a transformed cell with an expression vector containing a DNA sequence encoding said serine protease as set forth in FIG. 1 and a signal peptide sequence.

5. An isolated serine protease precursor having a serine protease signal peptide operable linked to an N-terminus of a serine protease produced by culturing a transformed cell with an expression vector containing a DNA sequence encoding said serine protease precursor as set forth in FIG. 6.

6. A serine protease precursor according to claim 5 wherein the expression vector contains the sequence as set forth in FIG. 7.

7. A process for preparing a serine protease which comprises culturing a transformed cell with an expression vector containing a serine protease gene encoding an amino acid sequence as set forth in FIG. 1.

8. A process according to claim 7 wherein the expression vector contains the sequence as set forth in FIG. 2.

9. A process for preparing a serine protease precursor having a serine protease signal peptide operably linked to an N-terminus of a serine protease produced by culturing a transformed cell with an expression vector containing a DNA sequence encoding said serine protease as set forth in FIG. 1 and a signal peptide sequence.

10. A process for preparing a serine protease precursor having a serine protease signal peptide operably linked to an N-terminus of a serine protease produced by culturing a transformed cell with an expression vector containing a DNA sequence encoding said serine protease precursor as set forth in FIG. 6.

11. A process according to claim 10 wherein the expression vector contains the sequence as set forth in FIG. 7.

12. An isolated serine protease gene encoding a serine protease, wherein said serine protease has the amino acid sequence as set forth in FIG. 1.

13. An isolated serine protease precursor gene encoding a serine protease precursor having a signal peptide operably linked to the N-terminal end of a serine protease of a polypeptide having an amino acid sequence as set forth in FIG. 1.

14. An isolated serine protease gene according to claim 13 containing a DNA nucleotide sequence as set forth in FIG. 2.

15. An isolated serine protease precursor gene according to claim 12 containing a DNA nucleotide sequence as set forth in FIG. 7.

* * * * *

UNITED STATES PATENT AND TRADEMARK OFFICE
CERTIFICATE OF CORRECTION

PATENT NO. : 5,661,000
DATED : August 26, 1997
INVENTOR(S) : Yosuke Aoki, Kiyoshi Okano, Masanobu Naruto, Hirohiko Shimizu and Haruji Nakamura It is certified that error appears in the above-indentified patent and that said Letters Patent is hereby corrected as shown below:

In Column 14, line 2, please change "A composition" to --An isolated composition--;
line 3, please change "coding" to --encoding--;
line 4, please change "A serine" to --An isolated serine--; and
line 54, please change "13" to --12--.

Signed and Sealed this

Second Day of December,1997

Attest:

BRUCE LEHMAN

Attesting Officer

Commissioner of Patents and Trademarks